United States Patent [19]

Isaacs et al.

[11] Patent Number: 4,980,165
[45] Date of Patent: Dec. 25, 1990

[54] PHARMACEUTICAL FORMULATIONS OF PLASMINOGEN ACTIVATOR PROTEINS

[75] Inventors: Benjamin S. Isaacs, Tewksbury; Himakshi Patel, Lowell, both of Mass.

[73] Assignee: Genetics Institute, Inc., Cambridge, Mass.

[21] Appl. No.: 302,846

[22] Filed: Jan. 27, 1989

[51] Int. Cl.$^5$ ............................................ A61K 37/547
[52] U.S. Cl. ................................ 424/94.64; 424/94.63
[58] Field of Search ............................ 424/94.64, 94.63

[56] References Cited

U.S. PATENT DOCUMENTS

| | | | |
|---|---|---|---|
| 4,244,943 | 1/1981 | Yamahira et al. | 424/94.63 |
| 4,505,893 | 3/1985 | Mori et al. | 424/94.64 |
| 4,650,678 | 3/1987 | Fuhge et al. | 514/588 |
| 4,777,043 | 10/1988 | Bennett et al. | 424/94.64 |
| 4,857,320 | 8/1989 | Wittwer | 424/94.63 |
| 4,898,826 | 2/1990 | Duffy et al. | 435/226 |

FOREIGN PATENT DOCUMENTS

| | | |
|---|---|---|
| 17322 | 12/1988 | Australia . |
| 211592 | 2/1987 | European Pat. Off. . |
| 217379 | 4/1987 | European Pat. Off. . |
| 2176702 | 1/1987 | United Kingdom . |
| 2176703 | 1/1987 | United Kingdom . |
| 1389 | 3/1987 | World Int. Prop. O. .......... 435/212 |

*Primary Examiner*—Jacqueline Stone
*Attorney, Agent, or Firm*—Bruce Eisen; Luann Cserr; Brian O'Shaughnessy

[57] ABSTRACT

Pharmaceutical formulations for intravenous bolus injection are presented that provide thrombolytic proteins, especially "second generation" tPA molecules, in relatively high concentrations at low concentrations of excipients.

17 Claims, No Drawings

PHARMACEUTICAL FORMULATIONS OF PLASMINOGEN ACTIVATOR PROTEINS

BACKGROUND

This invention relates to pharmaceutical compositions containing tPA or thrombolytic variants thereof. Such thrombolytic proteins are described, e.g. in U.S. Pat. application Ser. No. 825,104, filed 31 Jan. 1986; U.S. Ser. No. 853,781, filed 18 Apr. 1986; U.S. Ser. No. 861,699, filed 9 May 1986; U.S. Ser. No. 882,051, filed 2 July 1986, and PCT/US87/00257, filed 30 Jan. 1987.

Human tPA is known to have low solubility in the standard pharmaceutically acceptable excipients, most of which provide solubilities of less than 1 mg/ml. Others do not provide appreciable solubilities (>1 mg/ml) without an undesirable increase in ionic concentration.

That low solubility phenomenon has made compounding human tPA into efficacious pharmaceutical formulations problematic. See, e.g. U.S. Pat. No. 4,777,043 (Genentech), GB No. 2 176 702 and GB No. 2 176 703 (Wellcome) and EP No. 211 592 (SmithKline). The Genentech patent relates to formulations of tPA containing 0.02M to 1M arginine. We have found that creatinine also exhibits an appreciable solubilizing effect (>1 mg/ml) on plasminogen activator proteins. Notably, however, both of those excipients exhibit low thrombolytic solubility (<1 mg/ml) at excipient concentrations of 0.1M and less. The other applications relate to low pH formulations of tPA.

Relatively concentrated formulations, containing at least about 2.5 mg of protein/ml, are particularly desirable for bolus injection of thrombolytic proteins, and would therefore be especially appropriate for "second generation" tPA proteins such as ΔFE-1X (discussed infra.).

One advantage of such "second generation" compounds is that they have longer in vivo half lives than human tPA and may accordingly be administered as an intravenous bolus injection. In contrast, human tPA, which has a much shorter half-life, is administered as a continuous infusion over an extended period of time. Consequently, second generation plasminogen activators may be administered more rapidly and easily. Those advantages are particularly significant when, as with thrombolytics, administration of the therapeutic is a matter of life and death.

Bolus injection is practicable only if sufficiently concentrated formulations of the active agent are available. Furthermore, concentrated formulations are desirable to minimize the volume to be administered, and hence the time required to perform the injection.

Low excipient concentration is also desirable in formulations for IV bolus injection. High excipient concentration may increase osmolarity and tonicity of the formulation. Hypertonic solutions are deleterious to red blood cells and may cause patient discomfort, thus they should be administered more slowly. See Avis et al. *Pharmaceutical Dosage Forms: Parenteral Medications,* Vol. I, 168ff (1984). Pharmaceutical formulations that are isoosmotic and isotonic with respect to blood are preferred for rapid administration.

New formulations of thrombolytic proteins are clearly desirable. Ideally, such formulations would permit compounding the therapeutic protein in relatively high concentration with low concentration of excipients, provide enhanced protein stability, enhance the bioavailability of the protein, reduce costs of compounding the protein and improve the ease of administration of the pharmaceutical formulation.

THE INVENTION

We have discovered a new series of formulations that provide relatively high concentrations of tPA, or preferably "second generation" thrombolytic proteins, in the presence of surprisingly low concentrations of excipients. The pharmaceutical formulations of the present invention comprise pharmaceutical formulations comprising a therapeutically effective amount of a plasminogen activator; about 0.1M to about 0.5M histidine; and about 0.1M to about 0.5M creatinine. We further contemplate formulations comprising a therapeutically effective amount of a plasminogen activator; about 0.01M to about 0.5 M creatinine and about 0.1M to about 0.5M of a pharmaceutically acceptable excipient selected from the group consisting of proline and choline.

A therapeutically effective amount of a plasminogen activator protein for purposes of the present invention is at least about 2.5 to 6 mg/ml.

The excipients referred to above should be pharmaceutically acceptable excipients as well as cardiovascular therapy compatible excipients that are free of contraindications.

A list of exemplary excipients having a secondary, tertiary or quaternary amine functional group includes histidine (his), arginine, creatinine, proline (pro), betaine, choline, imidazole and tryptophan. Additionally, citrulline, while not presently a pharmaceutically acceptable excipient, is also an effective solubilizing agent. Preferred excipients containing a secondary, tertiary or quaternary amine functional group include histidine and creatinine.

A list of exemplary excipients that possess a negative net charge at about neutral pH, i.e. pH 6.0–7.5, includes glutamic acid (glu [−1]), aspartic acid (−1), succinic acid (−2), citric acid (−3), and sodium phosphate (NaPO4 [−3]). Preferred excipients possessing a negative net charge at about neutral pH, i.e. 6.0–7.5, are citric acid and glutamic acid.

An exemplary reagent having an amine functional group and a net positive charge at pH 6.0–7.5 that effectively solubilizes thrombolytic proteins is ethyl glycinate.

Additionally, the pharmaceutical formulations of the present invention may further comprise one or more excipients selected from the group consisting of: glycine (gly), propylene glycol (PG) and polyethylene glycol (PEG).

All excipients should be USP grade or pharmaceutical grade or National Formulary (NF) grade.

A pharmaceutical formulation for intravenous bolus injection having a therapeutically effective amount of a plasminogen activator generally comprises at least about 2.5–6 mg/ml of the thrombolytic protein, depending on the specific activity of the protein. More preferably, such a formulation comprises about 6 mg/ml or more of the thrombolytic protein. However, lower concentrations may be used in routes of administration other than bolus injection, e.g. IV drip or other modes of administration of extended duration. Effective amounts of the above excipients are from about 0.01M to about 0.5M. Preferred amounts of those excipients are from about 0.01M to about 0.1M. For example, one especially preferred pharmaceutical formulation comprises 0.05M each of histidine, citrate, and creatinine. The solubility of ΔFE1X in that formulation is at least about 6 mg/ml.

Other presently preferred pharmaceutical formulations for compounding second generation thrombolytic proteins are the following: (Formulation #147 [F147]) 0.05M his, 0.05M citrate and 0.05M glu; (F70) 0.1M his, 0.1M citrate and 0.1M creatinine; (F143) 0.05M citrate and 0.05M creatinine; (F128) 0.1M his, ? .1M glu and 0.1M creatinine; (134) 0.1M glu and 0.1M creatinine; (F146) 0.05M his, 0.05M gly and 0.05M citrate; (F138) 0.1M his and 0.1M creatinine.

Other formulations for compounding second generation thrombolytic proteins are disclosed in Tables I–V. The recited solubilities of thrombolytic proteins in those formulations are not necessarily maximum solubilities, but only indicate that the formulations have met arbitrarily targeted concentrations.

We contemplate that the inclusion of sugars, e.g. sucrose, and sugar alcohols, e.g. mannitol, may improve the stability of the thrombolytic proteins in the formulations of the present invention. Such sugar-stabilized formulations should contain about 1–10%, by weight, of the desired sugar or sugar alcohol.

The thrombolytic proteins used in the pharmaceutical formulations of the present invention preferably comprise a human tPA peptide sequence modified by deletion or replacement of one or more amino acid residues, especially within the amino terminal portion of the protein spanning the fibronectin finger homologous region, the epidermal growth factor homologous region and the first kringle region. One or more of the consensus N-linked glycosylation sites may be abolished and the plasmin cleavage site at which one-chain tPA is cleaved to form two-chain tPA may be modified to prevent or be resistant to such cleavage. Additionally, several amino acid residues may be deleted or replaced at the C-terminus of the protein. Proteins which may be formulated in accordance with this invention thus include human tPA, recombinant human tPA, variants lacking part or all of the peptide region from the N-terminus through kringle-1, and partially-glycosylated or non-glycosylated forms of the preceding. Especially preferred proteins lack 1–86 amino acids of human tPA and are further modified such that they lack one, two or three of the N-linked glycosylation sites which may be occupied by carbohydrate moieties in human tPA. Especially preferred proteins are referred to as ΔFE-3X and ΔFE-1X, and may be prepared as described in U.S. Ser. No. 882,051, filed 7 July 1986 and PCT/US87/00257, filed 30 Jan. 1987. ΔFE-3X lacks amino acids 5–86 and contains a glutamic acid residue in place of asparagine at position 117, relative to human tPA. ΔFE-1X lacks amino acids 5–86 and contains glutamic acid residues in place of asparagines at positions 117, 184 and 448. Both compounds have been previously described, as have variants lacking all N-terminal peptide sequence through kringle 1. The thrombolytic proteins may also be derivatized, e.g. acylated, to provide conjugates. See, e.g. Australian patent application No. AU-A-55514/86, EP-A-O No. 155 388, No. EP-A-0 152,736, EPA No. 85308533.0, EpA No. 85308534.8, and EPA No. 0 196 920. Those conjugates may then be formulated in accordance with the present invention. All of these compounds are believed to share sufficient common structural features as to be amenable to formulation using the materials and methods described herein.

In order to formulate thrombolytic proteins in accordance with this invention the protein may be obtained in a buffered aqueous solution. Such buffers may comprise those used to purify the protein, e.g. relatively concentrated salt solutions or arginine, as is known in the art. The thrombolytic protein may then be transferred to the formulation solution of choice by dialysis.

In order to compound the thrombolytic proteins, e.g. ΔFE1X and ΔFE3X, into the formulations of the present invention by dialysis three objectives must be met; (1) introduction of the excipients into the buffered protein solution, which solution may comprise, e.g. 0.5M arginine and 10mM phosphate at pH 7.5, (2) removal of arginine from the resulting solution without removing the excipients, and (3) ensure that substantially all, if not all, the arginine is removed.

Those objectives may be met by employing the following exemplary procedure: Step I: 5 mls of a thrombolytic protein solution containing 5–6 mg/ml of ΔFE1X or ΔFE3X in 0.5M–0.6M arginine and phosphate or Tris buffered to pH 6.0–7.5 is dialyzed against 500–1000 mls of buffer containing the excipients for any one of the formulations described below, and arginine at 0.2–0.5 M, pH 6.0–7.5. The dialysis may be carried out at room temperature or at 4° C. Step II: The excipients of step I are equilibrated with the protein solution. Arginine is then removed by dialysis against 1000–2000 mls of an arginine-less buffer solution of identical composition to that of Step I at pH 6.0–7.5. Step III: Repeat step II with fresh 1000–2000 mls of arginine-less buffer. This procedure, as well as others disclosed herein, may be also be conducted on larger scales.

Alternatively, buffer exchange may be accomplished through gel filtration, diafiltration or hydrophobic interaction chromatography in accordance with methods that are known in the art. For example, buffer exchange via gel filtration may be accomplished by passing a solution of ΔFE1X or ΔFE3X in arginine buffer over a gel column equilibrated with the formulation of choice. Hydrophobic interaction chromatography may be performed as follows: the protein, in 0.5M arginine-phosphate pH 7.5, is bound to a hydrophobic resin (e.g. Toyo Pearl Butyl [TSK Corp.] and Phenyl-Sepharose [Pharmacia]). The resin is then washed free of arginine and the protein is dislodged from the column by the formulation buffer.

The resulting thrombolytic pharmaceutical formulations may be lyophilized to provide a freeze-dried cake for later reconstitution with Water For Injection. The lyophilization may be carried out in accordance with the procedure described in U.S. Ser. No. 197,499, filed May 23, 1988, which is incorporated herein by reference. Where formulations are to be lyophilized, supplemental excipients, e.g. bulking agents, should be added. Such supplemental excipients include glycine, creatinine, and sodium phosphate.

Compounding thrombolytic proteins, e.g. ΔFE1X and ΔFE3X, into the pharmaceutical formulations of the present invention may be accomplished by dialysis as described in the following Example.

EXAMPLE

Dialysis to Compound Thrombolytic Proteins

Step I: 5 mls of a thrombolytic protein solution containing 4.5 mg/ml of ΔFE1X in 0.5M arginine and phosphate buffered to pH 7.5 was dialyzed against 1000 mls of buffer containing 0.1M histidine, 0.1 M citrate, 0.1M creatinine and arginine at 0.2M, pH 6.0. The dialysis was carried out at 4° C.

Step II: The excipients of step I were allowed to equilibrate with the protein solution. The protein solution was then dialyzed against 2000 mls of an arginine-less buffer solution of otherwise identical composition to that of Step I at pH 6.0.

Step III: Step II was repeated with fresh 2000 mls of arginineless buffer.

TABLE I
Exemplary Formulations for ΔFE1X

| Formulation # | Contents | Solubility* (mg/ml) |
|---|---|---|
| F92 | 0.1 M each of his and citrate | 6.0 |
| F141 | 0.05 M of each of his and citrate | 5.6 |
| F154 | 0.05 M of each of his and citrate and 0.1 M creatinine | TBD |
| F135 | 0.1 M each of his and citrate and 0.1 M glu | 5.7 |
| F147 | 0.05 M each of his and citrate and 0.05 M glu | 5.8 |
| F113 | 0.1 M each of his and citrate and 0.01 M creatinine | 6.2 |
| F70 | 0.1 M each of his and citrate and creatinine | 6.4 |
| F132 | 0.05 M each of his and citrate and creatinine | 6.0 |
| F136 | 0.1 M each of citrate and creatinine | 5.0 |
| F143 | 0.05 M each of citrate and creatinine | 5.3 | his = l-histidine; glu = l-glutamic acid; and gly = l-glycine
*Solubility data may not be maximum solubility.
TBD = To be determined

TABLE II
Exemplary Formulations for ΔFE1X

| Formulation # | Contents | Solubility* (mg/ml) |
|---|---|---|
| F102 | 0.1 M each of his and glu | 5.6 |
| F142 | 0.05 M of each of his and glu | 1.0 |
| F100 | 0.1 M of each of his and glu and 0.1 M gly | 5.0 |
| F145 | 0.05 M each of his, glu and gly | 2.5 |
| F153 | 0.1 M each of his and glu and 0.01 M creatinine | 5.4 |
| F128 | 0.1 M each of his and glu and creatinine | 6.0 |
| F133 | 0.05 M each of his and glu and creatinine | 3.0 |
| F134 | 0.1 M each of glu and creatinine | 5.7 |
| F152 | 0.05 M each of glu and creatinine | 5.0 |

TABLE III
Exemplary Formulations for ΔFE1X

| Formulation # | Contents | Solubility* (mg/ml) |
|---|---|---|
| F109 | 0.1 M each of his, gly and citrate | 5.0 |
| F146 | 0.05 M each of his, gly and citrate | 5.0 |
| F138 | 0.1 M each of his and creatinine | 5.0 |
| F131 | 0.1 M each of his, gly and creatinine | 2.8 |
| F155 | 0.1 M each of proline and citrate | 4.5 |

TABLE IV
Exemplary Formulations for ΔFE1X

| Formulation # | Contents | Solubility* (mg/ml) |
|---|---|---|
| F149 | 0.1 M each of his, gly, glu and PO4 | 5.0 |
| F150 | 0.05 M each of his, gly, glu and PO4 | 5.0 |
| F89 | 0.1 M his, gly, citrate and PO4 | 5.0 |
| F151 | 0.05 M his, gly, citrate and PO4 | 5.0 |

PO4 = sodium phosphate

TABLE V
Exemplary Formulation

| Contents | Formulation # | Solubility* ΔFE3X mg/ml | Solubility* ΔFE1X mg/ml |
|---|---|---|---|
| 0.5 M citrulline | F18 | 6 | |
| 0.1 M citrulline, his, citrate | F107 | 3.75 | |
| 0.1 M his, gly, glu | F100 | 1.42 | 2.9 |
| 0.2 M his. gly & 0.05 M glu | F116 | 1.9 | |
| 0.2 M his, gly & 0.05 M glu & 5% PG | F122 | 3.0 | |
| 0.1 M his & citrate | F106/92 | 2.6 | |
| 0.1 M his & citrate + 5% PG | F124 | 2.7 | |
| 0.2 M his & 0.1 M citrate | F96 | 3.9 | |
| 0.2 M his & 0.01 M citrate | F114 | 1.6 | |
| 0.2 M his & 0.1 M glu | F119 | 2.1 | |
| 0.2 M his & 0.1 M glu + 5% PG | F120 | 2.75 | |
| 0.2 M his & 0.1 M glu & PO4 | F95 | 3.3 | |
| 0.2 M his, 0.1 M glu & PO4 + 5% PG | F123 | 3.4 | |
| 0.1 M his, citrate, glycine | F109 | 2.77 | |
| 0.1 M his, citrate, glycine + 5% PG | F125 | 3.2 | |
| 0.1 M his, cit, gly, PO4 | F89 | 1.72 | 3.7 |
| 0.1 M his, cit, gly, PO4 + 1% PG | F118 | 1.96 | |
| 0.5 M creatinine | F48 | 4.0 | |
| 0.2 M creatinine & 0.1 M citrate | F126 | 3.5 | |
| 0.1 M creatinine, his, citrate | F70 | 3.74 | |
| 0.01 M creat, 0.1 M his, cit | F113 | 1.54 | 3.5 |
| 0.1 M ethyl glycinate, his, cit | F97 | 3.9 | |
| 0.1 M creatinine, his EDTA | F87 | 4.45 | |

PG = Propylene glycol

What is claimed is:

1. A thrombolytic composition comprising a therapeutically effective amount of a plasminogen activator in an aqueous parenteral formulation containing a solubilizing concentration of histidine and creatinine.

2. A composition of claim 1 wherein said concentration is about 0.01M to about 0.5M each of histidine and creatinine.

3. A composition of claim 2 wherein said concentration is about 0.1M of each histidine and creatinine.

4. A composition of claim 1 wherein said formulation additionally includes a solubilizing concentration of citrate ion.

5. A composition of claim 4 wherein said concentration is about 0.01 to about 0.5M each of histidine, citrate ion and creatinine.

6. A composition of claim 4 wherein said concentration is about 0.05M each of histidine, citrate ion and creatinine.

7. A composition of claim 1 wherein said formulation additionally includes a solubilizing concentration of glutamine.

8. A composition of claim 7 wherein said concentration is about 0.1M each of histidine, creatinine and glutamine.

9. A thrombolytic composition comprising a therapeutically effective amount of a plasminogen activator in an aqueous parenteral formulation containing a solubilizing concentration of histidine and citrate ion.

10. A composition of claim 9 wherein said formulation additionally includes a solubilizing concentration of an excipient selected from the group consisting of glutamine and glycine.

11. A composition 10 wherein said concentration is about 0.05 to about 0.1M each of histidine, citrate ion and either glutamine or glycine.

12. A composition of claim 10 wherein said concentration is about 0.05 to about 0.1M each of histidine, citrate ion and glycine.

13. A thrombolytic composition comprising a therapeutically effective amount of a plasminogen activator in an aqueous parenteral formulation containing a solubilizing concentration of creatinine and an excipient selected from the group consisting of citrate ion, glutamine, proline and choline.

14. A composition of claim 13 wherein said excipient is citrate ion and said concentration is about 0.05M each of creatinine and citrate ion.

15. A composition of claim 13 wherein said excipient is glutamine and said concentration is about 0.1M each of creatinine and glutamine.

16. A composition of claim 13 wherein said excipient is proline and said concentration is about 0.01M to about 0.5M each of creatinine and proline.

17. A composition of claim 13 wherein said excipient is choline and said concentration is about 0.01M to about 0.5M each of creatinine and choline.

* * * * *